(12) United States Patent
Agterberg et al.

(10) Patent No.: US 6,323,341 B1
(45) Date of Patent: Nov. 27, 2001

(54) PROCESS FOR THE CONTINUOUS PURIFICATION OF CRUDE ε-CAPROLACTAM

(75) Inventors: Frank P. W. Agterberg, Nieuwstadt; Rudolf P. M. Guit, Maastricht; Nicolaas F. Haasen, Limbricht, all of (NL)

(73) Assignees: DSM N.V., Heerlem (NL); E. I. Du Pont de Nemours & Company, Wilmington, DE (US)

( * ) Notice: Subject to any disclaimer, the term of this patent is extended or adjusted under 35 U.S.C. 154(b) by 0 days.

(21) Appl. No.: 09/665,592

(22) Filed: Sep. 19, 2000

Related U.S. Application Data

(63) Continuation of application No. PCT/NL99/00148, filed on Mar. 17, 1999.

(30) Foreign Application Priority Data

Mar. 20, 1998 (EP) .................................................. 98200875

(51) Int. Cl.[7] .................................................. C07D 201/16
(52) U.S. Cl. .................................................. 540/540
(58) Field of Search .................................................. 540/540

(56) References Cited

U.S. PATENT DOCUMENTS

| 3,761,467 | * | 9/1973 | Williams et al. | 260/239.3 A |
| 4,248,781 | | 2/1981 | Horn et al. | 260/239.3 |
| 4,900,821 | | 2/1990 | Tan et al. | 540/540 |
| 5,496,941 | | 3/1996 | Ritz et al. | 540/540 |

FOREIGN PATENT DOCUMENTS

| 564528A | 7/1975 | (CH) . |
| 1022591B | 1/1958 | (DE) . |
| 1620756 | 7/1970 | (DE) . |
| 826665 | 3/1998 | (EP) . |
| 7-179419 | 7/1995 | (JP) . |

* cited by examiner

*Primary Examiner*—Bruck Kifle
(74) *Attorney, Agent, or Firm*—Pillsbury Winthrop LLP

(57) ABSTRACT

The invention relates to a process for the purification of crude ε-caprolactam, wherein crude ε-caprolactam prepared by cyclization of alkyl 6-aminocaproate, 6-aminocapronitrile, 6-aminocaproic acid, 6-aminocaproic amide and/or oligomers thereof, is subjected to a crystallization process.

8 Claims, No Drawings

PROCESS FOR THE CONTINUOUS PURIFICATION OF CRUDE ε-CAPROLACTAM

This application is a cont. of PCT/NL99/00148 filed Mar. 17, 1999.

The invention relates to a process for the purification of crude ε-caprolactam.

Such a process is known from U.S. Pat. No. 5,496,941. This patent publication describes the continuous purification of crude ε-caprolactam by hydrogenation, subsequent treatment in an acid medium and subsequent distillation in an alkaline medium. The treatment in the acid medium can be carried out in two ways:
(1) by passing the hydrogenation product, in a solvent, over an ion exchanger containing terminal acid groups, or
(2) by distilling the hydrogenation product in the presence of sulphuric acid.

The process results in a treated product, from which impurities like cyclic nitrites, amines and imines are removed.

A disadvantage of the process from U.S. Pat. No. 5,496,941 is that crude ε-caprolactam prepared by cyclization of alkyl 6-aminocaproate, 6-aminocapronitrile, 6-aminocaproic acid, 6-aminocaproic amide and/or oligomers thereof, such as for instance described in WO-A-9837063, cannot be effectively purified with this method.

We have found that this is caused by the fact that ε-caprolactam prepared by cyclization contains small amounts of N-substituted or C-substituted lactams and/or amides and these cannot be effectively removed with the above known method. Other processes to prepare ε-caprolactam e.g. according to Beckmann rearrangement result in crude ε-caprolactam containing a different pattern of impurities.

An object of the invention is to provide a purification process for crude ε-caprolactam prepared by cyclization of alkyl 6-aminocaproate, 6-aminocapronitrile, 6-aminocaproic acid, 6-aminocaproic amide and/or oligomers thereof.

This object is achieved in that the crude ε-caprolactam is subjected to a crystallization process.

We have found that according to the invention an increased purity can be obtained, which cannot be attained according to the above known purification process.

It is believed that also other known methods to purify ε-caprolactam prepared by cyclization of alkyl 6-aminocaproate, 6-aminocapronitrile, 6-aminocaproic acid, 6-aminocaproic amide and/or oligomers thereof, e.g. by extraction, do not result in sufficiently purified caprolactam. Due to the fact that the type of the impurities of the crude ε-caprolactam was unknown and that these impurities are present in low levels in the crude ε-caprolactam, at which level their behaviour in purification steps cannot be predicted, the success of the process according to the invention could not be foreseen.

Preferably the crystallization process comprises the following steps:
(1) liquid crude ε-caprolactam is fed into a crystallizer
(2) in the crystallizer conditions are set such that ε-caprolactam crystals and a mother liquid are formed
(3) a stream from the crystallizer is fed to a separator where the ε-caprolactam crystals are separated from the mother liquid
(4) the mother liquid is recycled.

In step (2) the crystallizer is operated such that crystallization of ε-caprolactam occurs through cooling. In the crystallizer relatively pure ε-caprolactam crystals are formed (solid phase) and a mother liquid, which comprises ε-caprolactam, impurities and optionally solvent (liquid or melt phase). The solid phase in the crystallizer can have a different appearance, depending on the way the crystallization is performed. The crystallization in step (2) can be performed either by cooling via a heat exchanging surface (suspension or layer crystallization) or by adiabatic cooling by evaporation of part of the contents of the crystallizer, for instance a solvent, under reduced pressure (crystallization in suspension). The method of crystallization induced by reduced pressure cooling is preferred, since no crystallization on inner surfaces of the crystallizer occurs. In reduced pressure cooling the condensed vapour from the crystallizer may or may not be returned, totally or partially to the contents of the crystallizer. Preferably the crystallizer is operated by evaporating the solvent under reduced pressure.

Preferably solvent is present in the mixture in the crystallizer, although crystallization can also be conducted without solvent. Many solvents are suitable. Examples of suitable solvents are water, alkanes (like n-hexane, n-heptane, iso-octane, cyclohexane), alcohols (like methanol, ethanol, n-propanol, butanol), aromatic hydrocarbons (like benzene, toluene, o-xylene, m-xylene, p-xylene), ammonia, chlorinated hydrocarbons (like tetrachloromethane, chloroform or ethylchloride), ketones (like acetone or methylethyl keton) and esters (like ethyl acetate). Preferably water and aromatic hydrocarbons are used as solvent, since these solvents give large crystals. Most preferred as solvent is water. The solvent will act as a freezing point depressor for the melt in the crystallizer.

The concentration of solvent in the melt in the crystallizer is dependent on the solvent, the amounts of impurities in the feed caprolactam and the way the cooling in the crystallizer is performed. With the preferred solvent water and reduced pressure cooling the concentration water in the melt is usually below 20 weight %, preferably 1–15 weight % and more preferred 2–10 weight %.

A solvent stream may be directly fed to the crystallizer and/or is mixed with the liquid crude caprolactam feed stream prior to being fed to the crystallizer.

The temperature of the mixture in the crystallizer is dependent on the presence and concentration of solvent and impurities in the mixture, but at most 69° C., being the melting temperature of pure ε-caprolactam. Preferably the temperature of mixture in the crystallizer is 20–69° C., more preferable 35–67° C. The crystallizer can be operated in batch or in continuous mode. Preferably the crystallizer is operated in a continuous mode.

The separator in step (3) may be any separator that is capable of separating crystals from the mother liquid, e.g. a filter working under forces like gravity, reduced pressure, increased pressure or a centrifuge. Various types of filters and centrifuges can be used. In these separators during or after separation washing of the crystals is possible and preferred. The separator in step (3) is for instance a horizontal vacuum belt filter. This type of solid-liquid separator has an excellent washing efficiency. Another example of a separator is a crystal washcolumn, in which the crystals are compacted into a packed bed which bed is transported with gravity, hydraulic pressure or a mechanical means. An example of a crystal washcolumn in which the crystal bed is transported with a mechanical means is a Niro screw-type wash column system as for example described in 'European Chemical News', Jun. 30–Jul. 6, 1997, page 23. A crystal washcolumn has the advantage that an effective separation of the ε-caprolactam crystals from the mother liquid is achieved and simultaneously very effective washing of the crystals is performed. A more preferred crystal washcolumn is the so-called TNO-Thijssen hydraulic wash column as described in "Improved procedures for separating crystals for the melt", D. Verdoes, G. J. Arkenbout et al., Applied Thermal Engineering, 17 (8–10), 1997, 879–888.

In the TNO-Thijssen hydraulic wash column, the purified ε-caprolactam crystals are removed from the crystal bed and subsequently molten by a heat exchanger. A part of the molten ε-caprolactam crystals is recycled to the crystal washcolumn as washing liquid. The ε-caprolactam washing liquid finally crystallizes on the surface of ε-caprolactam crystals present in the so-called washfront. This is advantageous because, with a minimum quantity of washing liquid, a very effective separation of the ε-caprolactam crystals from the mother liquid and simultaneously a high washing efficiency of the ε-caprolactam crystals is achieved. In the TNO-Thijssen hydraulic wash column the purified ε-caprolactam is obtained as a liquid melt.

Advantageously the purified ε-caprolactam from step (3) is further purified in a second crystallization step (2b) followed by a second separation/washing step (3b) of the ε-caprolactam crystals. This second crystallization step (2b) may be performed in a similar way as the first crystallization step (2). The separation and effective washing of the ε-caprolactam crystals from the mother liquid can be performed in a solid-liquid separation equipment as described for separation/washing step (3). If necessary additional crystallization steps and separation/washing steps are possible.

The mother liquid can be recycled in step (4) according to known methods. Advantageously the mother liquid of the first crystallization step is recycled after the main part of the impurities originating from the crude caprolactam are removed from the mother liquid. Impurities may be separated from the mother liquid by distillation, extraction or crystallization, or any separation technique known to a person skilled in the art. Also chemical treatment of the mother liquid, e.g. by hydrogenation or an ion exchange treatment, as part of a process to remove the impurities from the mother liquid are possible. The purified mother liquid stream may be recycled as a solvent stream to one or more crystallizers. The mother liquid of the second or subsequent crystallization steps may be pure enough to be recycled to earlier crystallization steps without treatment.

Preferably the mother liquid from the second crystallization step (2b) is recycled to the first crystallization step (2).

The liquid crude ε-caprolactam to be fed to the crystallization process in step (1) can be prepared from an ε-caprolactam process stream, from a process in which ε-caprolactam is prepared by cyclization of 6-amino caproate, 6-amino capronitrile, 6-aminocaproic acid, 6-amino caproic amide and/or oligomers thereof, e.g. as described in WO-A-9837063. Such ε-caprolactam process stream will typically contain a light fraction, with compounds having a lower boiling point than caprolactam, e.g. light organics and a heavy fraction with compounds of higher boiling point than ε-caprolactam, e.g. ε-caprolactam cyclic oligomers. Preferably the light fractions and heavy fractions are separated from the ε-caprolactam process stream to give the crude ε-caprolactam to be fed to the crystallization section. This separation can be done with conventional techniques, for instance by distillation.

The invention will be elucidated by the following examples and comparative experiments, however these are not intended to limit the scope of the invention in any way.

EXAMPLE I 73.6 grams of crude ε-caprolactam was obtained by cyclization of a mixture of 6-aminocaproic acid, 6-aminocaproic amide and oligomers thereof and also some caprolactam at 300° C. as described in example IX of WO-A-9837063. The crude ε-caprolactam contained 6345 ppm of N-methyl caprolactam, 100 ppm of methyl-valerolactam and 78 ppm of valeramide among other impurities, and was purified by melt crystallization according to the following procedure. Water was added to the crude caprolactam, to obtain a mixture containing 10 wt. % water. The mixture was heated to 50° C. to obtain a homogeneous melt. Subsequently the temperature was slowly reduced to 30° C. with a rate of approximately 10° C. per hour, while stirring mechanically. During the cooling down a caprolactam crystals slurry was formed. When the temperature had reached 30° C. the crystals were separated by means of filtration, and subsequently washed 2–3 times with a saturated aqueous solution of caprolactam.

33.7 grams of pure caprolactam crystals were obtained, containing 51 ppm of N-methyl caprolactam, 1 ppm methyl-valerolactam and 1 ppm of valeramide. Specifications were determined by the followings methods:

The E290 is 0.14, VB is 0.7 meq/kg. The E290 and VB values were measured according to the procedure described at the end of this experimental section. This single-step crystallization procedure resulted in purified product which meets the E290 specification, and almost meets the VB specification for caprolactam obtained by Beckmann rearrangement.

EXAMPLE II

The product of example I was recrystallized by the same procedure. The product contains 2 ppm of N-methyl caprolactam, 1 ppm of methyl-valerolactam and <1 ppm of valeramide. E290 is 0.02, VB is <0.4 meq/kg. This example shows that by means of two crystallization steps pure caprolactam can be obtained which meets the VB specification for caprolactam obtained by Beckmann rearrangement.

EXAMPLE III

Example I was repeated, with the exception that lights and heavies were removed from the crude caprolactam by distillation over a short vigreux column prior to the crystallization. 45.7 grams of distilled caprolactam, containing 2121 ppm of N-methyl caprolactam, 85 ppm of methyl-valerolactam and 69 ppm of valeramide among other impurities, was crystallized. 23.8 grams of pure caprolactam crystals were obtained, containing 39 ppm of N-methyl caprolactam, 1 ppm of methyl valerolactam and 2 ppm of valeramide. The addition of the distillation prior to crystallization results in a further improvement of the E(290) to 0.05 and VB to 0.41 meq/kg compared to a single-step crystallization procedure, and results in a product which meets the E290 and VB specifications.

Comparative Experiment A

Crude caprolactam as described in example II of WO-A-9817642 was purified by a continuous extraction with 4-methyl-2-pentanol as described in the same example. The purified caprolactam was isolated by distilling the 4-methyl-2-pentanol solvent from the resulting caprolactam solution. The purified product contains 2050 ppm of N-methyl caprolactam, 110 ppm of methyl-valerolactam and 530 ppm of valeramide, showing that this extraction does not effectively remove these impurities.

Comparative Experiment B

The product obtained from comparative experiment A was further purified by removing lights and heavies by means of a continuous distillation over a Spalt column. The purified caprolactam contains 47 ppm of N-methyl caprolactam, 110 ppm of methyl-valerolactam and 437 ppm of valeramide. This indicates that straightforward distillation cannot remove the latter compound to a sufficiently low level.

Comparative Experiment C

The same crude caprolactam as used for example I was treated as described in U.S. Pat. No. 5,496,941. An aqueous caprolactam solution was hydrogenated, passed over an acidic ion exchanger and finally distilled in the presence of NaOH. The purified product contains 3033 ppm of N-methyl caprolactam, 96 ppm opf methyl-valerolactam and 540 ppm of valeramide. Although E(290) of 0.05 meets the specifications for caprolactam obtained by Beckmann rearrangement, the VB of 9 meq/kg is clearly way off from the desired specification.

Determination of the specifications was carried out in the following manner:

E290: Determination of the absorbance at a wavelength of 290 nm (E290) was carried out according to ISO method 7059, Caprolactam for industrial use—Determination of absorbance at a wavelength of 290 nm) by determination of the absorbance of a 50 wt. % caprolactam solution in water at 290 nm, using a quartz cell with 4 cm path length.

Volatile Bases (VB): (cf. ISO method 7059, Caprolactam for industrial use—Determination of volatile bases content—Titrimetric method after distillation) A test sample of caprolactam was distilled in an alkaline medium. The volatile bases were liberated from the sample, taken up in 0.01 N hydrochloric acid, and determined by titration with 0.01 N sodium hydroxide solution.

$$VB = (((V_0 - V_1) \times 0.01)/\text{grams sample}) \times 1000 \text{ meq/kg}$$

where $V_0$=volume, in milliliters, of the standard sodium hydroxide solution used in the blank test, and $V_1$=volume, in milliliters, of the standard sodium hydroxide solution used in the determination.

What is claimed is:

1. A process for the preparation of purified $\epsilon$-caprolactam comprising:
   i) cyclizing alkyl 6-aminocaproate, 6-aminocapronitrile, 6-aminocaproic acid, 6-aminocaproic amide and/or oligomers thereof to prepare a crude $\epsilon$-caprolactam; and
   ii) subjecting the crude $\epsilon$-caprolactam to a crystallization process.

2. A process according to claim 1, wherein the crystallization process comprises the following steps:
   (1) liquid crude $\epsilon$-caprolactam is fed into a crystallizer
   (2) in the crystallizer conditions are set such that $\epsilon$-caprolactam crystals and a mother liquid are formed
   (3) a stream from the crystallizer is fed to a separator where the $\epsilon$-caprolactam crystals are separated from the mother liquid
   (4) the mother liquid is recycled.

3. A process according to claim 2, wherein the crystallization in step (2) is crystallization in suspension which is effected through reduced pressure cooling.

4. A process according to claim 2, wherein the $\epsilon$-caprolactam crystals from step (3) are further purified in a second crystallization step (2b).

5. A process according to claim 4, wherein the crystallization in the second crystallization step (2b) is crystallization in suspension effected through reduced pressure cooling.

6. A process according to claim 5, wherein the mother liquid from the second crystallization step (2b) is recycled to the first crystallization step (2).

7. A process according to claim 2, wherein the liquid crude caprolactam is obtained from a previous process step in a caprolactam synthesis process after removal of heavy and light compounds by distillation.

8. A process according to claim 2, wherein the mother liquid is recycled in step (4) after the impurities originating from the crude caprolactam are removed from the mother liquid.

* * * * *